United States Patent
Han et al.

(10) Patent No.: US 11,974,883 B2
(45) Date of Patent: May 7, 2024

(54) ULTRASOUND IMAGING APPARATUS, METHOD OF CONTROLLING THE SAME, AND COMPUTER PROGRAM

(71) Applicant: SAMSUNG MEDISON CO., LTD., Hongcheon-gun (KR)

(72) Inventors: Songyi Han, Seoul (KR); Yeonah Kang, Seoul (KR); Jaesung Lee, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 150 days.

(21) Appl. No.: 17/133,741

(22) Filed: Dec. 24, 2020

(65) Prior Publication Data

US 2021/0236092 A1 Aug. 5, 2021

(30) Foreign Application Priority Data

Jan. 31, 2020 (KR) ........................ 10-2020-0012185

(51) Int. Cl.
*A61B 8/00* (2006.01)
*A61B 8/08* (2006.01)
(Continued)

(52) U.S. Cl.
CPC .............. *A61B 8/468* (2013.01); *A61B 8/085* (2013.01); *A61B 8/0866* (2013.01);
(Continued)

(58) Field of Classification Search
CPC ....... A61B 8/468; A61B 8/085; A61B 8/0866; A61B 8/0875; A61B 8/14; A61B 8/463;
(Continued)

(56) References Cited

U.S. PATENT DOCUMENTS

| 7,787,676 B2 | 8/2010 | Drobnitzky |
| 9,307,958 B2 | 4/2016 | Nishihara et al. |
| 9,805,466 B2 | 10/2017 | Ryu et al. |
| 10,169,641 B2 | 1/2019 | Lee et al. |

(Continued)

FOREIGN PATENT DOCUMENTS

| KR | 10-2017-0099222 A | 8/2017 |
| KR | 10-1868021 B1 | 6/2018 |

OTHER PUBLICATIONS

Krakow, D et al., Use of three-dimensional ultrasound imaging in the diagnosis of prenatal-onset skeletal dysplasias, 2003, Ultrasound Obstet Gynecol, 21, 467-472 (Year: 2003).*

(Continued)

*Primary Examiner* — Baisakhi Roy
*Assistant Examiner* — Kaitlyn E Sebastian
(74) *Attorney, Agent, or Firm* — Sughrue Mion, PLLC

(57) ABSTRACT

An ultrasound imaging apparatus includes: a probe configured to output ultrasound signals to an object and detect echo signals reflected from the object; a display; and at least one processor configured to generate a first ultrasound image based on the echo signals, detect at least one object of interest, each corresponding to a fetus's finger or toe in the first ultrasound image, and when the at least one object of interest is detected, place at least one arrow indicator outside a vicinity of a region of interest corresponding to the detected at least one object of interest, and orientate the at least one arrow indicator toward the region of interest.

18 Claims, 17 Drawing Sheets

(51) Int. Cl.
- *A61B 8/14* (2006.01)
- *G06T 7/00* (2017.01)
- *G06T 7/70* (2017.01)
- *G16H 15/00* (2018.01)
- *G16H 30/20* (2018.01)
- *G16H 30/40* (2018.01)

(52) U.S. Cl.
CPC .............. *A61B 8/0875* (2013.01); *A61B 8/14* (2013.01); *A61B 8/463* (2013.01); *A61B 8/469* (2013.01); *A61B 8/5207* (2013.01); *A61B 8/5223* (2013.01); *A61B 8/54* (2013.01); *G06T 7/0012* (2013.01); *G06T 7/70* (2017.01); *G16H 15/00* (2018.01); *G16H 30/20* (2018.01); *G16H 30/40* (2018.01); *G06T 2207/10132* (2013.01); *G06T 2207/30044* (2013.01); *G06T 2207/30242* (2013.01)

(58) Field of Classification Search
CPC ..... A61B 8/469; A61B 8/5207; A61B 8/5223; A61B 8/54; A61B 8/461; A61B 8/467; A61B 8/56; A61B 8/4477; A61B 8/4405; A61B 8/4427; A61B 8/464; G06T 7/0012; G06T 7/70; G06T 2207/10132; G06T 2207/30044; G06T 2207/30242; G16H 15/00; G16H 30/20; G16H 30/40
See application file for complete search history.

(56) References Cited

U.S. PATENT DOCUMENTS

| | | | |
|---|---|---|---|
| 10,631,825 | B2 | 4/2020 | Lee et al. |
| 2011/0125016 | A1* | 5/2011 | Lazebnik ............ A61B 5/1075 600/443 |
| 2014/0192054 | A1 | 7/2014 | Yoo et al. |
| 2014/0276057 | A1* | 9/2014 | Lee ........................ A61B 8/463 600/440 |
| 2015/0164475 | A1 | 6/2015 | Kuga et al. |
| 2016/0042525 | A1* | 2/2016 | Lee ..................... G06V 20/647 382/103 |

OTHER PUBLICATIONS

Database Medline, US National Library of Medicine (NLM), Aug. 1995 (XP002803049), and Bronshtein et al., "Transvaginal Sonographic Diagnosis of Fetal Finger Abnormalities in Early Gestation," American Institute of Ultrasound in Medicine, Journal of Ultrasound in Medicine, vol. 14, No. 8, pp. 591-595, Aug. 1995 (XP002803199), Total 6 pages.

Bromley et al., Pictorial Essay "Abnormalities of the Hands and Feet in the Fetus: Sonographic Findings," American Roentgen Ray Society, AJR, No. 165, pp. 1239-1243, Nov. 1995 (XP055806393).

Hata et al., "Three-dimensional ultrasonographic assessment of fetal hands and feet," Ultrasound in Obstetrics and Gynecology, vol. 12, No. 4, pp. 235-239, Oct. 1998 (XP055806395), Total 6 pages.

Communication dated Jun. 23, 2021, issued by the European Patent Office in counterpart European Application No. 20216470.3.

Communication dated Jul. 4, 2023 by the European patent Office in counterpart European Patent Application No. 20216470.3.

* cited by examiner

ULTRASOUND IMAGING APPARATUS, METHOD OF CONTROLLING THE SAME, AND COMPUTER PROGRAM

CROSS-REFERENCE TO RELATED APPLICATION(S)

This application is based on and claims priority under 35 U.S.C. § 119 to Korean Patent Application No. 10-2020-0012185, filed on Jan. 31, 2020, in the Korean Intellectual Property Office, the disclosure of which is incorporated by reference herein in its entirety.

BACKGROUND

1. Field

The disclosure relates to ultrasound imaging apparatuses, methods of controlling an ultrasound imaging apparatus, and computer programs for performing the methods.

2. Description of Related Art

Ultrasound imaging apparatuses have been widely used in obstetrics and gynecology (OB/GYN) to examine the condition of a fetus. During an OB/GYN examination, a user checks the number of fetal fingers and toes to diagnose deformities of the fetal fingers and toes. During a fetal ultrasound scan, the user may place indicators at positions corresponding to a fetus's fingers and toes on an ultrasound image, and after the ultrasound scan, the user may check the number and positions of the fetus's fingers and toes based on the ultrasound image for treatment. However, when placing indicators corresponding to the fingers and toes, the user may have difficulties placing the indicators at corresponding positions after changing a direction of the indicators according to a fetal position and a location of a structure. In particular, to display all indicators for fingers and toes on both hands and feet, frequent use of buttons is required, resulting in increased work fatigue and a long inspection time.

SUMMARY

Provided are an apparatus and method for automatically placing arrow indicators at positions corresponding to fetal fingers and toes, thereby increasing user convenience.

Additional aspects will be set forth in part in the description which follows and, in part, will be apparent from the description, or may be learned by practice of the presented embodiments of the disclosure.

In accordance with an aspect of the disclosure, an ultrasound imaging apparatus includes: a probe configured to output ultrasound signals to an object and detect echo signals reflected from the object; a display; and at least one processor configured to generate a first ultrasound image based on the echo signals, detect at least one object of interest, each corresponding to a fetus's finger or toe in the first ultrasound image, and when the at least one object of interest is detected, place at least one arrow indicator outside a vicinity of a region of interest corresponding to the detected at least one object of interest, and orientate the at least one arrow indicator toward the region of interest.

The at least one processor may be further configured to detect the at least one object of interest by detecting a shape of a finger bone or toe bone in the first ultrasound image.

The at least one processor may be further configured to recognize fingers that are the at least one object of interest when four or more shapes of finger bones are detected in the first ultrasound image and recognize toes that are the at least one object of interest when four or more shapes of toe bones are detected in the first ultrasound image.

The at least one object of interest may include a plurality of objects of interest, and the at least one processor may be further configured to place the at least one arrow indicator to be respectively directed toward the plurality of objects of interest in a direction perpendicular to a virtual line connecting the plurality of objects of interest with one another.

The at least one processor may be further configured to place the at least one arrow indicator on a region corresponding to an amniotic fluid in the first ultrasound image The at least one processor may be further configured to place, when four fingers or four toes are recognized in the first ultrasound image, a fifth arrow indicator in a direction of a thumb or big toe.

The at least one processor may be further configured to control the display to display the first ultrasound image and a second ultrasound image on the display, detect at least one object of interest in the second ultrasound image when four or fewer objects of interest are detected in the first ultrasound image, and place the at least one arrow indicator for the at least one object of interest detected in the second ultrasound image.

The ultrasound imaging apparatus may further include an input interface, and the at least one processor may be further configured to display the first ultrasound image and a second ultrasound image on the display, display on the first ultrasound image, when four or fewer objects of interest are detected in the first ultrasound image, first group arrow indicators respectively corresponding to the four or fewer objects of interest detected in the first ultrasound image and a second group arrow indicator visually represented in a different way from the first group arrow indicators, and place the second group arrow indicator on the second ultrasound image based on a user input for moving the second group arrow indicator, the user input being received via the input interface.

The at least one processor may be further configured to provide, via the display, information about whether each of ten (10) fingers on left and right hands and each of ten (10) toes on left and right feet have been recognized.

The at least one processor may be further configured to calculate information about reliability in detecting the at least one object of interest and display on the display the information about reliability of the at least one arrow indicator together with the at least one arrow indicator.

In accordance with another aspect of the disclosure, a method of controlling an ultrasound imaging apparatus includes: outputting ultrasound signals to an object and detecting echo signals reflected from the object; generating a first ultrasound image based on the echo signals; detecting at least one object of interest, each corresponding to a fetus's finger or toe in the first ultrasound image; when the at least one object of interest is detected, placing at least one arrow indicator outside a vicinity of a region of interest corresponding to the detected at least one object of interest, and orientating the at least one arrow indicator toward the region of interest.

In accordance with another aspect of the disclosure, a computer program is stored in a recording medium and includes at least one instruction which, when executed by a processor, causes the processor to perform methods of controlling an ultrasound imaging apparatus according to embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
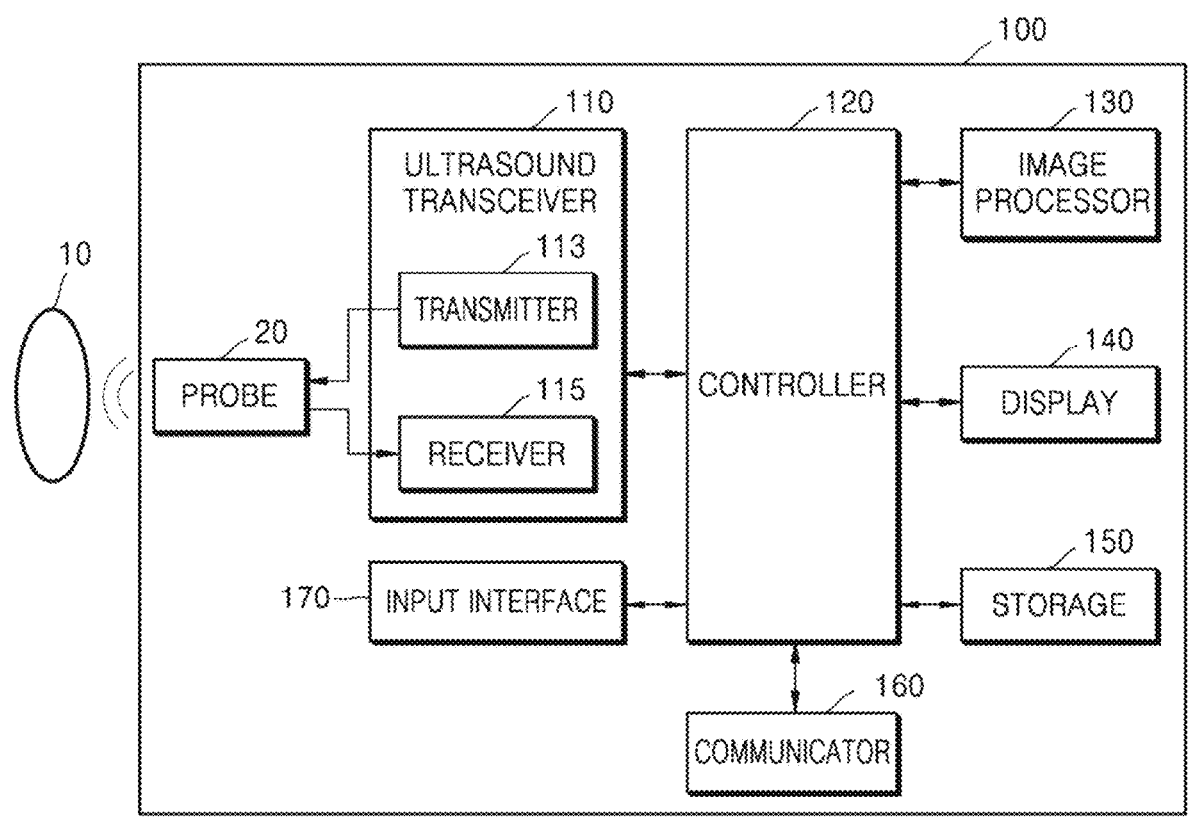
FIG. 1 is a block diagram of a configuration of an ultrasound imaging apparatus according to an embodiment of the disclosure.

Certain example embodiments are described in greater detail below with reference to the accompanying drawings.

In the following description, the same drawing reference numerals are used for the same elements even in different drawings. Matters defined in the description, such as detailed construction and elements, are provided to assist in a comprehensive understanding of the example embodiments. Thus, it is apparent that the example embodiments can be carried out without such specifically defined matters. Also, well-known functions or constructions are not described in detail so as not to obscure the example embodiments with unnecessary detail.

As used herein, the term "and/or" includes any and all combinations of one or more of the associated listed items. Expressions such as "at least one of," when preceding a list of elements, modify the entire list of elements and do not modify the individual elements of the list.

Terms such as "part" and "portion" as used herein denote those elements that may be embodied by software or hardware. According to example embodiments, a plurality of parts or portions may be embodied by a single unit or element, or a single part or portion may include a plurality of elements.

In example embodiments, an image may include any medical image acquired by various medical imaging apparatuses such as a magnetic resonance imaging (MRI) apparatus, a computed tomography (CT) apparatus, an ultrasound imaging apparatus, or an X-ray apparatus.

Also, in the present specification, an "object", which is a thing to be imaged, may include a human, an animal, or a part thereof. For example, an object may include a part of a human, that is, an organ or a tissue, or a phantom.

Throughout the specification, an ultrasound image refers to an image of an object processed based on ultrasound signals transmitted to the object and reflected therefrom.

FIG. 1 is a block diagram illustrating a configuration of an ultrasound imaging apparatus 100, i.e., a diagnostic apparatus, according to an example embodiment.

Referring to FIG. 1, the ultrasound diagnosis apparatus 100 may include a probe 20, an ultrasound transceiver 110, a controller 120, an image processor 130, one or more displays 140, a storage 150, e.g., a memory, a communicator 160, i.e., a communication device or an interface, and an input interface 170.

The ultrasound diagnosis apparatus 100 may be of a cart-type or a portable-type ultrasound diagnosis apparatus, that is portable, moveable, mobile, or hand-held. Examples of the portable-type ultrasound diagnosis apparatus 100 may include a smart phone, a laptop computer, a personal digital assistant (PDA), and a tablet personal computer (PC), each of which may include a probe and a software application, but embodiments are not limited thereto.

The probe 20 may include a plurality of transducers. The plurality of transducers may transmit ultrasound signals to an object 10 in response to transmission signals received by the probe 20, the transmission signals being from a transmitter 113. The plurality of transducers may receive ultrasound signals reflected from the object 10 to generate reception signals. In addition, the probe 20 and the ultrasound diagnosis apparatus 100 may be formed in one body (e.g., arranged in a single housing), or the probe 20 and the ultrasound diagnosis apparatus 100 may be formed separately (e.g., arranged separately in separate housings) but linked wirelessly or via wires. In addition, the ultrasound diagnosis apparatus 100 may include one or more probes 20 according to embodiments.

The controller 120 may control the transmitter 113 to generate transmission signals to be applied to each of the plurality of transducers based on a position and a focal point of the plurality of transducers included in the probe 20.

The controller 120 may control the ultrasound receiver 115 to generate ultrasound data by converting reception signals received from the probe 20 from analogue to digital signals and summing the reception signals converted into digital form, based on a position and a focal point of the plurality of transducers.

The image processor 130 may generate an ultrasound image by using ultrasound data generated from the ultrasound receiver 115.

The display 140 may display a generated ultrasound image and various pieces of information processed by the ultrasound diagnosis apparatus 100. The ultrasound diagnosis apparatus 100 may include two or more displays 140 according to the present example embodiment. The display 140 may include a touch screen in combination with a touch panel.

The controller 120 may control the operations of the ultrasound diagnosis apparatus 100 and flow of signals between the internal elements of the ultrasound diagnosis apparatus 100. The controller 120 may include a memory for storing a program or data to perform functions of the ultrasound diagnosis apparatus 100 and a processor and/or a microprocessor (not shown) for processing the program or data. For example, the controller 120 may control the operation of the ultrasound diagnosis apparatus 100 by receiving a control signal from the input interface 170 or an external apparatus.

The ultrasound diagnosis apparatus 100 may include the communicator 160 and may be connected to external apparatuses, for example, servers, medical apparatuses, and portable devices such as smart phones, tablet personal computers (PCs), wearable devices, etc., via the communicator 160.

The communicator 160 may include at least one element capable of communicating with the external apparatuses. For example, the communicator 160 may include at least one among a short-range communication module, a wired communication module, and a wireless communication module.

The communicator 160 may receive a control signal and data from an external apparatus and transmit the received control signal to the controller 120 so that the controller 120 may control the ultrasound diagnosis apparatus 100 in response to the received control signal.

The controller 120 may transmit a control signal to the external apparatus via the communicator 160 so that the external apparatus may be controlled in response to the control signal of the controller 120.

For example, the external apparatus connected to the ultrasound diagnosis apparatus 100 may process the data of the external apparatus in response to the control signal of the controller 120 received via the communicator 160.

A program for controlling the ultrasound diagnosis apparatus 100 may be installed in the external apparatus. The program may include command languages to perform some operations of the controller 120 or all operations of the controller 120.

The program may be pre-installed in the external apparatus or may be installed by a user of the external apparatus by downloading the program from a server that provides applications. The server that provides applications may include a recording medium where the program is stored.

The storage 150 may store various data or programs for driving and controlling the ultrasound diagnosis apparatus 100, input and/or output ultrasound data, ultrasound images, applications, etc.

The input interface 170 may receive a user's input to control the ultrasound diagnosis apparatus 100 and may include a keyboard, button, keypad, mouse, trackball, jog switch, knob, a touchpad, a touch screen, a microphone, a motion input device (, a biometrics input device, etc. For example, the user's input may include inputs for manipulating buttons, keypads, mice, trackballs, jog switches, or knobs, inputs for touching a touchpad or a touch screen, a voice input, a motion input, and a bioinformation input, for example, iris recognition or fingerprint recognition, but example embodiments are not limited thereto.

An example of the ultrasound diagnosis apparatus 100 according to the present example embodiment is described below with reference to FIGS. 2A, 2B, and 2C.

Figure 2A:
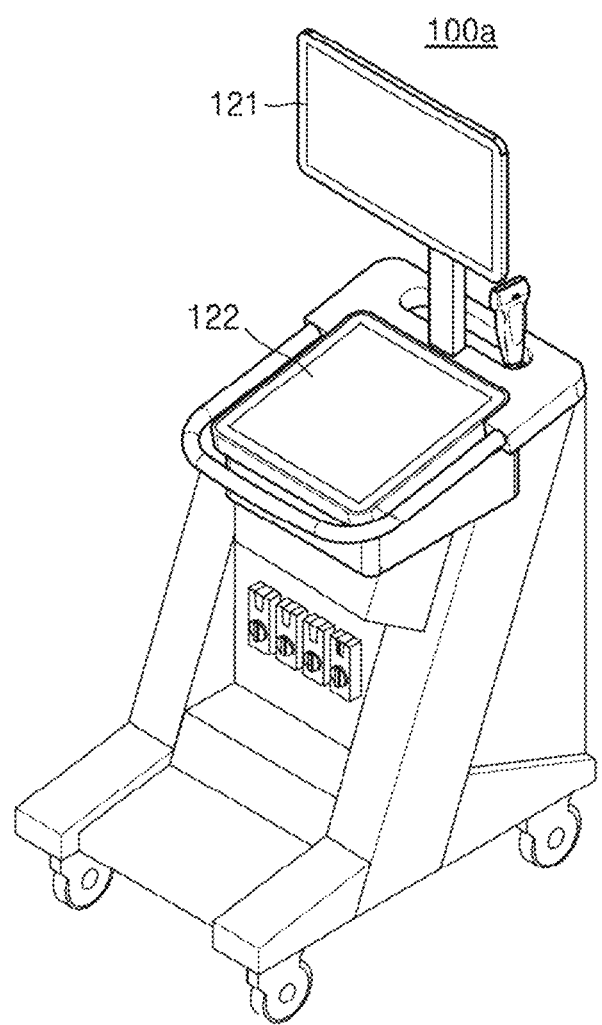
FIGS. 2A through 2C are diagrams illustrating ultrasound imaging apparatuses according to embodiments of the disclosure.
Figure 2B:
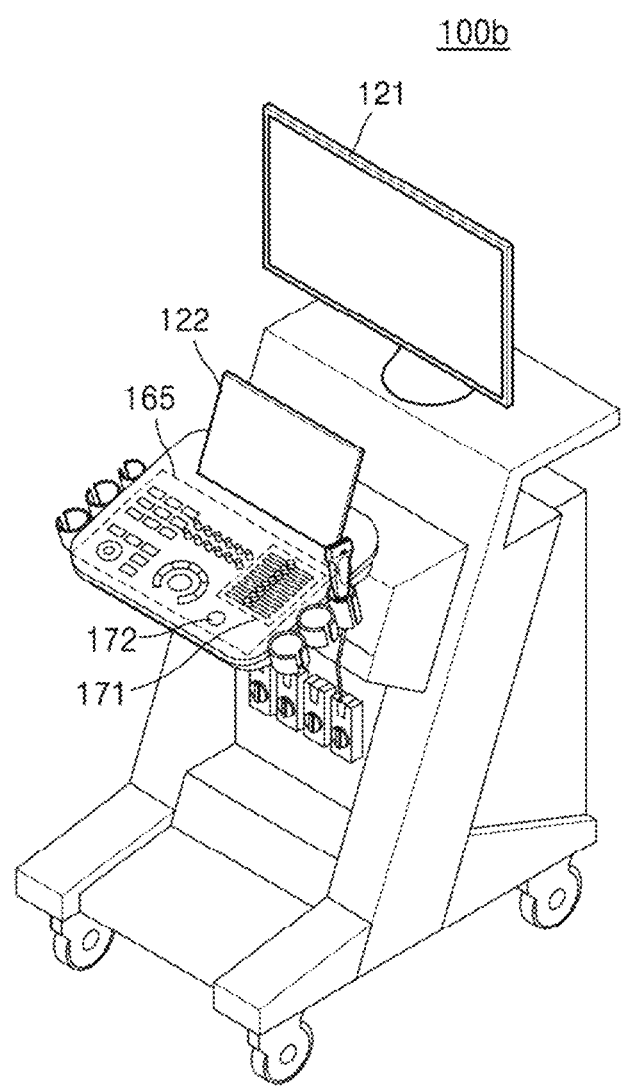
Figure 2C:
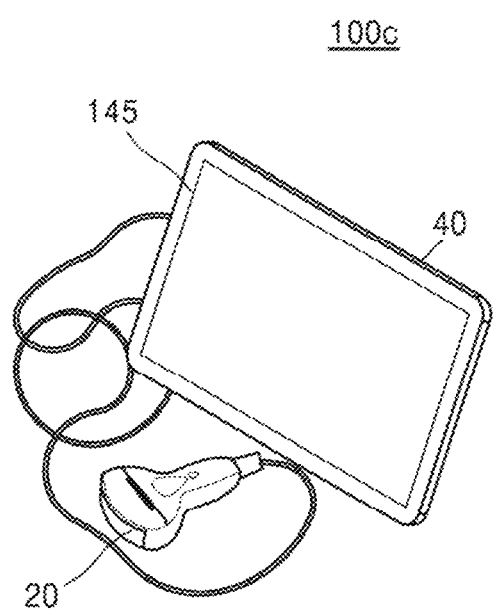

FIGS. 2A, 2B, and 2C are diagrams illustrating ultrasound diagnosis apparatus according to an example embodiment.

Referring to FIGS. 2A and 2B, the ultrasound diagnosis apparatus 100a and 100b may include a main display 121 and a sub-display 122. At least one among the main display 121 and the sub-display 122 may include a touch screen. The main display 121 and the sub-display 122 may display ultrasound images and/or various information processed by the ultrasound diagnosis apparatus 100a and 100b. The main display 121 and the sub-display 122 may provide graphical user interfaces (GUIs), thereby receiving user's inputs of data to control the ultrasound diagnosis apparatus 100a and 100b. For example, the main display 121 may display an ultrasound image and the sub-display 122 may display a control panel to control display of the ultrasound image as a GUI. The sub-display 122 may receive an input of data to control the display of an image through the control panel displayed as a GUI. The ultrasound diagnosis apparatus 100a and 100b may control the display of the ultrasound image on the main display 121 by using the input control data.

Referring to FIG. 2B, the ultrasound diagnosis apparatus 100b may include a control panel 165. The control panel 165 may include buttons, trackballs, jog switches, or knobs, and may receive data to control the ultrasound diagnosis apparatus 100b from the user. For example, the control panel 165 may include a time gain compensation (TGC) button 171 and a freeze button 172. The TGC button 171 is to set a TGC value for each depth of an ultrasound image. Also, when an input of the freeze button 172 is detected while scanning an ultrasound image, the ultrasound diagnosis apparatus 100b may continue displaying a frame image at that time point.

The buttons, trackballs, jog switches, and knobs included in the control panel 165 may be provided as a GUI to the main display 121 or the sub-display 122.

Referring to FIG. 2C, the ultrasound diagnosis apparatus 100c may include a portable device. An example of the portable ultrasound diagnosis apparatus 100c may include, for example, smart phones including probes and applications, laptop computers, personal digital assistants (PDAs), or tablet PCs, but example embodiments are not limited thereto.

The ultrasound diagnosis apparatus 100c may include the probe 20 and a main body 40. The probe 20 may be connected to one side of the main body 40 by wire or wirelessly. The main body 40 may include a touch screen 145. The touch screen 145 may display an ultrasound image, various pieces of information processed by the ultrasound diagnosis apparatus 100c, and a GUI.

Figure 3:
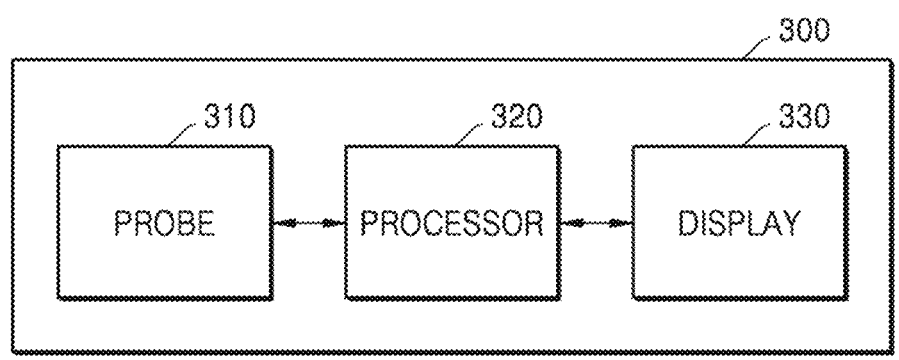
FIG. 3 is a block diagram of a configuration of an ultrasound imaging apparatus according to an embodiment of the disclosure.

FIG. 3 is a block diagram of a configuration of an ultrasound imaging apparatus 300 according to an embodiment of the disclosure.

According to an embodiment of the disclosure, the ultrasound imaging apparatus 300 includes a probe 310, a processor 320, and a display 330.

The probe 310 including an array of a plurality of transducers transmits ultrasound signals to an object and detects echo signals reflected from the object. The probe 310 may correspond to the probe 20 of FIG. 1. According to embodiments of the disclosure, the probe 310 may correspond to a two-dimensional (2D) probe having an array of one row of transducers, or a three-dimensional (3D) probe having a 2D array of m×n transducers (where m and n are natural numbers).

The processor 320 controls all operations of the ultrasound imaging apparatus 300. The processor 320 may be configured as one or more processors. The processor 320 receives ultrasound signals from the probe 310 to reconstruct an ultrasound image. The ultrasound signals generated by the probe 310 undergo predetermined signal processing via a beamformer, an amplifier, an analog-to-digital converter, etc., and are then transmitted to the processor 320. The processor 320 may perform a specific operation by executing an instruction or command stored in a memory.

The processor 320 generates a first ultrasound image based on echo signals. The first ultrasound image is obtained by performing ultrasound imaging of a fetus. The first ultrasound image may include an object of interest including a fetus's finger or toe. The processor 320 may define a region of interest (ROI) corresponding to the object of interest. The object of interest may be detected based on anatomical features of the fetus's finger or toe. For example, the processor 320 may detect an object of interest by detecting a shape corresponding to a bone of the finger or toe in the first ultrasound image. When four or more structures corresponding to bones of fingers are detected side by side, the processor 320 may recognize the corresponding structures as the fingers. Also, when four or more structures corresponding to bones of toes are detected side by side, the processor 320 may recognize the corresponding structures as the toes.

The processor 320 places an arrow indicator corresponding to the object of interest detected in the first ultrasound image such that the arrow indicator is directed toward an ROI corresponding to the object of interest. The arrow indicator is an indicator having an arrow shape, and start and end points of the arrow may be defined. The arrow indicator may be placed on the first ultrasound image such that its end point is directed toward the object of interest. The processor 320 may place the arrow indicator on a region contrasting with a color of the arrow indicator. For example, when the arrow indicator is white or red in color, the processor 320 may place the arrow indicator on an amniotic fluid region indicated in black.

The processor 320 may determine a direction and placement of the arrow indicator. The arrow indicator may be orientated to point toward a tip of a finger or toe while being placed outside the vicinity of the tip of the finger or toe. An end point of the arrow indicator is orientated toward the tip of the finger or toe.

The display 330 displays ultrasound images and predetermined data. The display 330 displays a graphical user interface (GUI) view of the ultrasound imaging apparatus 300. The display 330 may correspond to the display 140 of FIG. 1.

The display 330 displays the first ultrasound image and the arrow indicator placed on the first ultrasound image.

Figure 4:
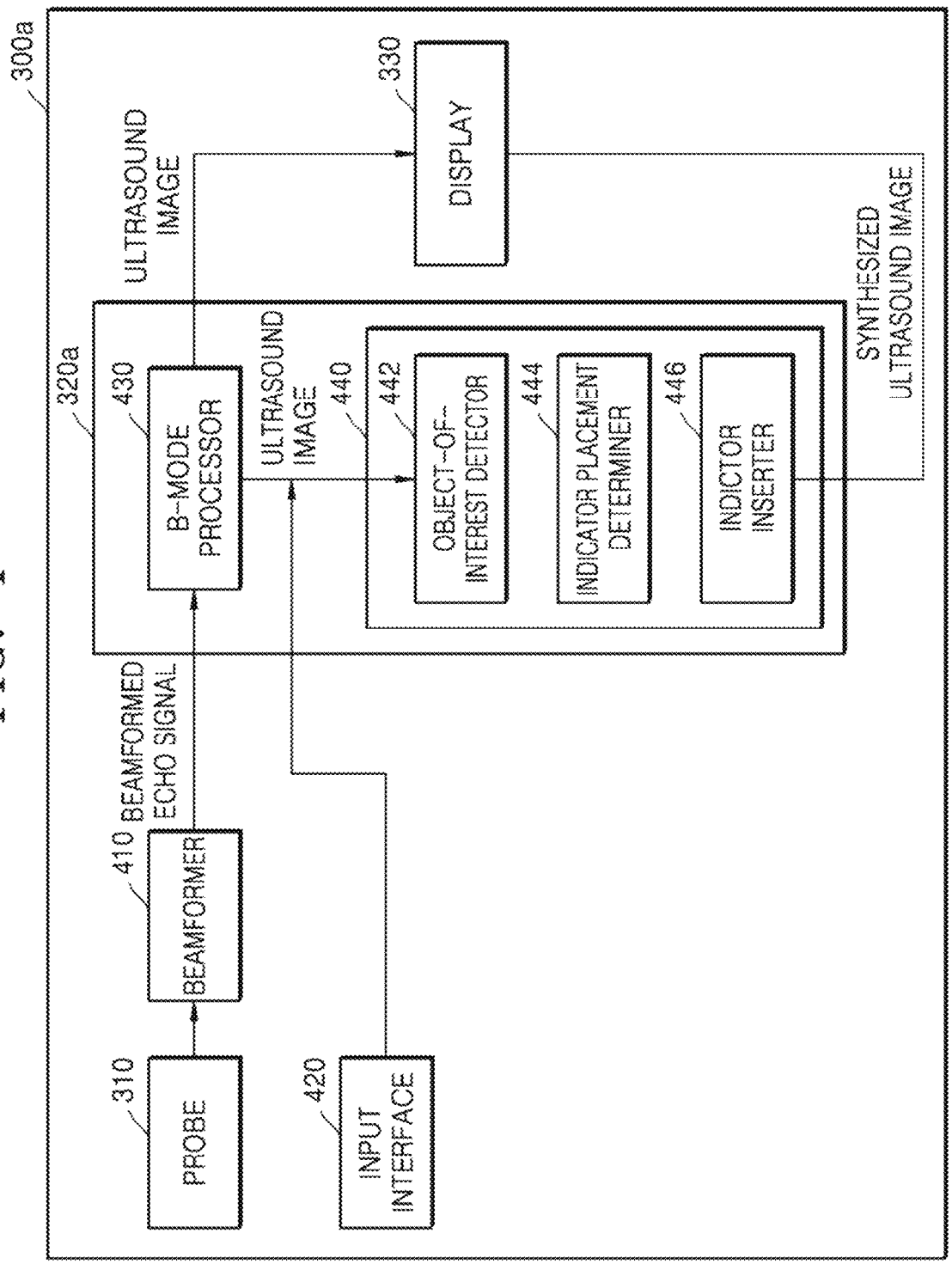
FIG. 4 is a block diagram of a configuration of an ultrasound imaging apparatus according to an embodiment of the disclosure.

FIG. 4 is a block diagram of a configuration of an ultrasound imaging apparatus 300a according to an embodiment of the disclosure.

According to an embodiment of the disclosure, the ultrasound imaging apparatus 300a may include a probe 310, a processor 320a, a display 330, a beamformer 410, and an input interface 420. The processor 320a includes a brightness (B)-mode processor 430 and an indicator placement processor 440.

Each block in FIG. 4 may correspond to a software block or hardware block executed by computer program code. The processor 320a may include various software or hardware blocks for an operation of the ultrasound imaging apparatus 300 as well as the B-mode processor 430 and the indicator placement processor 440.

Echo signals detected by the probe 310 are input to the beamformer 410. The beamformer 410 adjusts a phase of the echo signals to generate beamformed echo signals. The beamformer 410 may include a register and a delay circuit.

The beamformer 410 outputs the beamformed echo signals to the B-mode processor 430 of the processor 320a. The B mode processor 430 generates an ultrasound image, which is a B-mode image, based on the input echo signals. The B mode processor 430 outputs the ultrasound image to the indicator placement processor 440.

The indicator placement processor 440 may detect an object of interest corresponding to a finger or toe based on a control signal requesting finger/toe detection and input from the input interface 420 and place an arrow indicator. For example, the control signal requesting finger/toe detection may be input in the form of a user input for selecting a hand/foot capture mode, a user input for requesting execution of an automatic finger/toe detection function, etc. The indicator placement processor 440 includes an object-of-interest detector 442, an indicator placement determiner 444, and an indicator inserter 446.

The object-of-interest detector 442 detects an object of interest corresponding to a finger or toe in an ultrasound image. An operation of the object-of-interest detector 442 is now described with reference to FIG. 5.

Figure 5:
FIG. 5 is a diagram for describing a process of detecting an object of interest, according to an embodiment of the disclosure.

FIG. 5 is a diagram for describing a process of detecting an object of interest, according to an embodiment of the disclosure.

The object-of-interest detector 442 detects an object of interest 520 corresponding to a finger or toe in a first ultrasound image 510. The object-of-interest detector 442 may detect the object of interest 520 based on anatomical features of the finger or toe. For example, the object-of-interest detector 442 may detect positions of bones of fingers or toes based on bright echo signals from the bones of fingers or toes. Because bones are generally represented by bright gray-level values in an ultrasound image, the object-of-interest detector 442 may detect the bones of fingers and toes based on a shape of a region having bright gray-level values.

The object-of-interest detector 442 may detect the object of interest 520 when the bones of fingers or toes are adjacent to one another so a predetermined number or more of the bones are detected. Because a bone of a finger or toe is positioned close to that of a neighboring finger or toe, the object-of-interest detector 442 may detect the object of interest 520 based on such arrangement of the fingers or toes. When there is only a single finger bone or toe bone, it is difficult to determine that its shape corresponds to a finger or toe. Only when a predetermined number or more of shapes of finger bones or toe bones are arranged parallel to one another, the object-of-interest detector 442 may determine the corresponding shapes as being fingers or toes, thereby improving the accuracy of detecting fingers or toes. For example, only when four or more shapes of finger bones or toe bones are arranged parallel to one another, the object-of-interest detector 442 may determine the corresponding shapes as being fingers or toes.

The object-of-interest detector 442 may define a predetermined region of a distal phalange of a finger or toe as being the object of interest 520. For example, the object-of-interest detector 442 may define a predetermined region adjacent to a tip of a distal phalange of a finger or toe as being a region corresponding to the object of interest 520.

An operation of the indicator placement determiner 444 is now described with reference to FIGS. 4 and 6.

Figure 6:
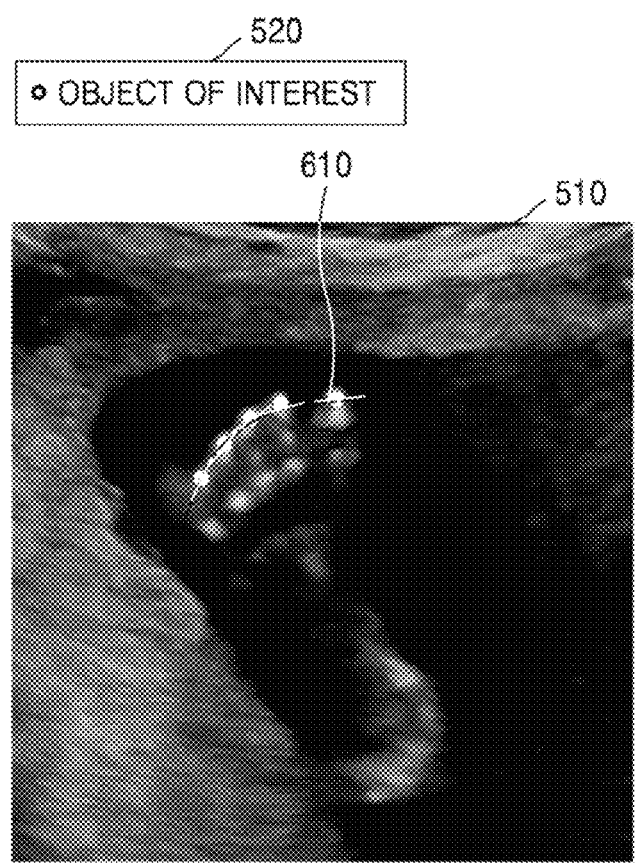
FIG. 6 is a diagram for describing an operation of an indicator placement determiner according to an embodiment of the disclosure.

FIG. 6 is a diagram for describing an operation of the indicator placement determiner 444 according to an embodiment of the disclosure.

The indicator placement determiner 444 determines the placement of an arrow indicator corresponding to an object of interest detected by the object-of-interest detector 442. Referring to FIG. 6, the indicator placement determiner 444 may determine the placement of an arrow indicator such that the arrow indicator is directed toward each object of interest 520. According to an embodiment, the indicator placement determiner 444 determines a virtual line 610 connecting objects of interest 520 detected side by side. Next, the indicator placement determiner 444 determines a direction of an arrow indicator such that the arrow indicator is placed for each object of interest 520 in a direction perpendicular to the virtual line 610. Furthermore, the indicator placement determiner 444 determines a position of an arrow indicator for each object of interest 520 such that an end point of the arrow indicator is located a predetermined distance from a region corresponding to the object of interest 520. An arrow indicator may be orientated in a direction from an amniotic fluid towards a bone of each finger or toe.

According to an embodiment, when four objects of interest 520 are detected in an ultrasound image 510, the indicator placement determiner 444 places four first group arrow indicators respectively corresponding to the four objects of interest 520 while additionally placing a second group arrow indicator that is a fifth one. The second group arrow indicator may be additionally placed on the ultrasound image 510 to be adjacent to the first group arrow indicators respectively corresponding to the four objects of interest 520. For example, the second group arrow indicator may be placed in a direction of a thumb or big toe. Furthermore, the second group arrow indicator may have different display attributes than the first group arrow indicators respectively corresponding to the four objects of interest 520. For example, the second group arrow indicator may be displayed with a different color or a different type of line (a dotted line, a solid line, a dash-dotted line, or the like) from the first group arrow indicator. When detecting a fetus's fingers in an ultrasound image, only the remaining fingers, except for the thumb, may be commonly seen according to a direction in which the ultrasound image is captured, a fetus's position, etc. Thus, according to an embodiment, the second group arrow indicator may be placed in the direction of the thumb even when the thumb is not seen, thereby allowing the user to easily recognize the direction of the thumb.

According to an embodiment, when more than five fingers or toes are detected in the ultrasound image 510, the indicator placement determiner 444 places five arrow indicators in a sequential manner from the thumb or big toe to the little finger or toe. The indicator placement determiner 444 may automatically select not to place an arrow indicator for the remaining finger or toe other than the five fingers or toes. As another example, the indicator placement determiner 444 may place, for the remaining extra finger or toe, an arrow indicator having different display attributes from the five arrow indicators arranged in the sequential manner from the thumb or big toe. According to the embodiment, when examining an ultrasound image in which a deformity where the number of fingers or toes per hand exceeds 5 is seen, the user directly diagnoses the deformity in the fetus.

An operation of the indicator inserter 446 is now described with reference to FIGS. 4 and 7.

Figure 7:
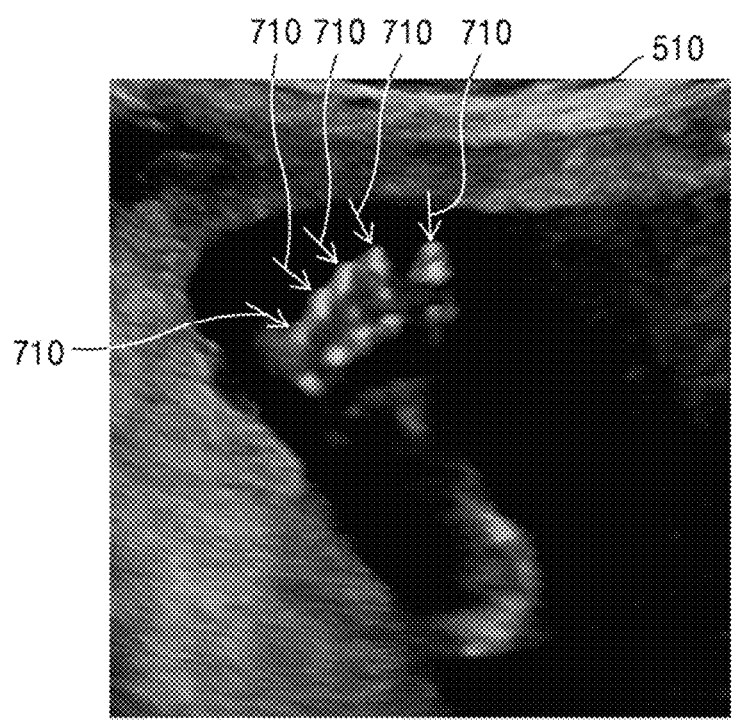
FIG. 7 is a diagram for describing an operation of an indicator inserter according to an embodiment of the disclosure.

FIG. 7 is a diagram for describing an operation of the indicator inserter 446 according to an embodiment of the disclosure.

The indicator inserter 446 inserts a plurality of arrow indicators 710 into an ultrasound image 510 according to a position and a direction of each arrow indicator 710, which are determined by the indicator placement determiner 444. The arrow indicators 710 may have an arrow shape with a predetermined color. For example, each arrow indicator 710 may be displayed by a white arrow.

According to an embodiment, the arrow indicators 710 may be synthesized into the ultrasound image 510. The arrow indicators 710 respectively corresponding to the objects of interest 520 are respectively placed at positions and in directions determined by the indicator placement determiner 444, and the indicator inserter 446 may change pixel values of the ultrasound image 510 in a state in which the arrow indicators 710 are placed on the ultrasound image 510, such that the arrow indicators 710 may be synthesized in the ultrasound image 510 Furthermore, the processor 320a may store, in a storage, an ultrasound image generated by synthesizing the arrow indicators 710 and the ultrasound image 510.

According to another embodiment, the arrow indicators 710 are placed on the ultrasound image 510 in a different layer from the ultrasound image 510, and the arrow indicators 710 may be inserted into or removed from the ultrasound image 510 according to a specific user input. Furthermore, the processor 320a may store, in the storage, the ultrasound image 510 together with information about the arrow indicators 710. The information about the arrow indicators 710 may include information about the number of arrow indicators 710 and a position and a direction of each arrow indicator 710. When the information about the arrow indicators 710 is stored together with the stored ultrasound image 510, the processor 320a may display the information about the arrow indicators 710 together with the ultrasound image 510, and insert the arrow indicators 710 into or remove them from the ultrasound image 510 according to a user input.

Referring back to FIG. 4, the display 330 displays in real-time a B-mode ultrasound image output from the B-mode processor 430 during scanning. Furthermore, the display 330 displays an ultrasound image obtained by synthesizing an ultrasound image and an arrow indicator.

Figure 8:
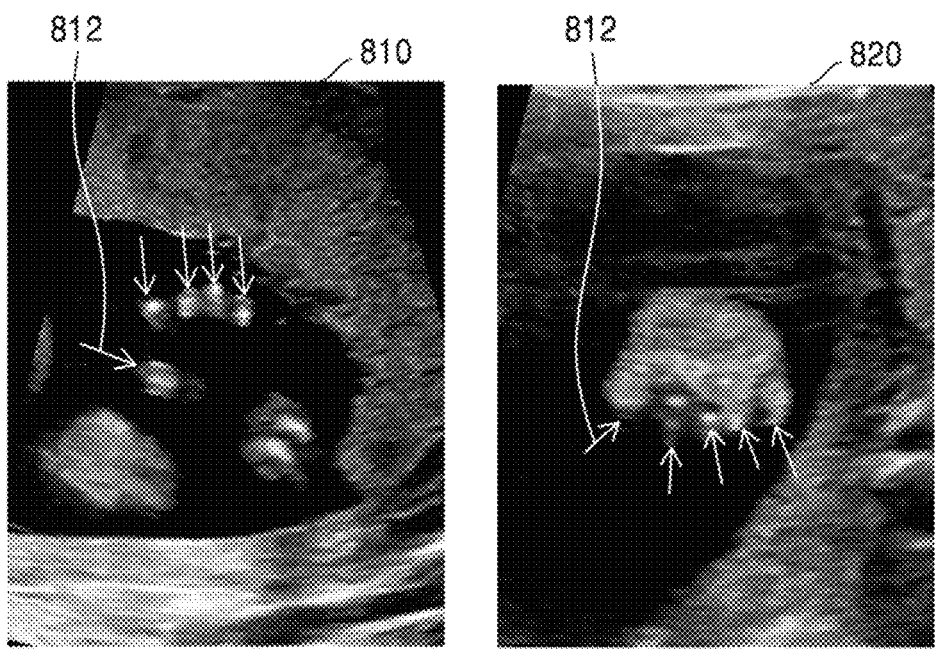
FIG. 8 illustrates a case in which objects of interest are detected in an ultrasound image, according to an embodiment of the disclosure.

FIG. 8 illustrates a case in which objects of interest are detected in an ultrasound image, according to an embodiment of the disclosure.

According to an embodiment of the disclosure, when five fingers or five toes are all detected in an ultrasound image, a plurality of arrow indicators 812 are respectively placed for the five fingers or toes.

All five fingers are detected in an ultrasound image 810, and the arrow indicators 812 were respectively placed for the five fingers. The arrow indicators 812 may have the same display attributes for all the five fingers or have different display attributes for each of the thumb, index finger, middle finger, ring finger, and little finger.

All five toes are detected in an ultrasound image 820, and the arrow indicators 812 are respectively placed for the five toes. The arrow indicators 812 may have the same display attributes for the five toes, or have different display attributes for each of the big toe, index toe, middle toe, ring toe, and little toe.

Figure 9:
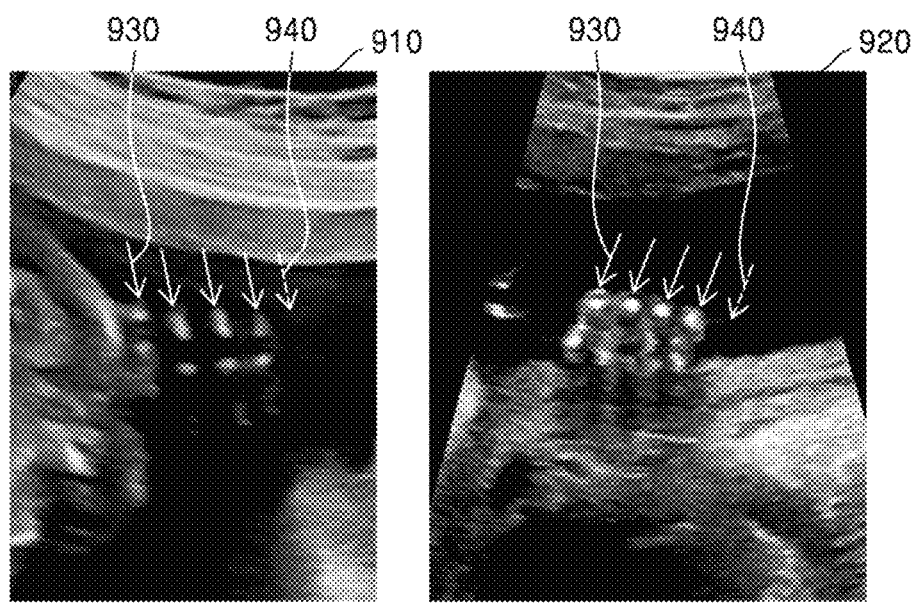
FIG. 9 illustrates a case in which objects of interest are detected in an ultrasound image, according to an embodiment of the disclosure.

FIG. 9 illustrates a case in which objects of interest are detected in an ultrasound image, according to an embodiment of the disclosure.

When four fingers and four toes are respectively detected in ultrasound images 910 and 920, the ultrasound imaging apparatus 300 may place and display first group arrow indicators 930 on the ultrasound image 910 or 920 for the detected four fingers or toes while additionally placing and displaying a second group arrow indicator 940 thereon. In detail, when the four fingers are detected in the ultrasound image 910, the first group arrow indicators 930 are placed and displayed on the ultrasound image 910 for the four fingers while the second group arrow indicator 940 is further displayed thereon in the direction of the thumb. Similarly, when the four toes are detected in the ultrasound image 920, the first group arrow indicators 930 are displayed on the ultrasound image 920 for the four toes while the second group arrow indicator 940 is further displayed thereon in the direction of the big toe. The first group arrow indicators 930 have different display attributes from the second group arrow indicator 940. According to an embodiment, the second group arrow indicator 940 may be moved or removed according to a user input received via an input interface.

When an ultrasound image of a fetus is captured, in many cases, not all five fingers are visible in the ultrasound image because the fetus is hiding a hand or clenching a fist. Because the fetus often bends only the thumb, or the thumb is likely to be invisible due to a scanning direction, there are many cases that only the four fingers are seen but the thumb is not visible. According to embodiments of the disclosure, when four fingers and four toes are respectively detected in the ultrasound images 910 and 920, the ultrasound imaging apparatus 300 may display the second group arrow indicator 930 in the direction of the thumb or big toe, thereby allowing the user to predict a location of the finger or toe that is not easily detected.

Figure 10:
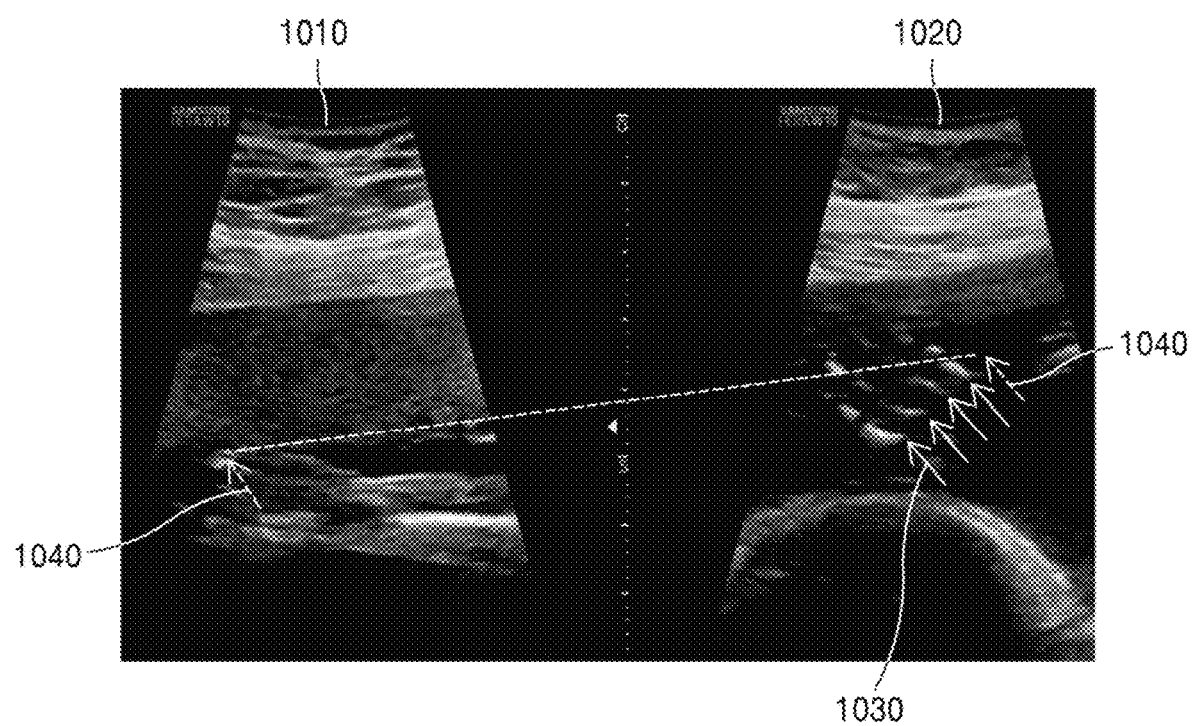
FIG. 10 illustrates an operation of an ultrasound imaging apparatus according to an embodiment of the disclosure.

FIG. 10 illustrates an operation of the ultrasound imaging apparatus 300 according to an embodiment of the disclosure.

According to an embodiment of the disclosure, the ultrasound imaging apparatus 300 displays first and second ultrasound images 1020 and 1010 together on a screen. The first and second ultrasound images 1020 and 1010 may correspond to various combinations of a stored ultrasound image and a real-time scan image. For example, the first ultrasound image 1020 may be a stored ultrasound image, and the second ultrasound image 1010 may be a real-time scan image. The user may freeze the second ultrasound image 1010 by using a freeze function.

When four or fewer objects of interest are detected in the first ultrasound image 1020, first group arrow indicators 1030 and a second group arrow indicator 1040 may be displayed on the first ultrasound image 1020. The user may move the second group arrow indicator 1040 to the second ultrasound image 1010 via the input interface. For example, the second group arrow indicator 1040 may be moved with a trackball, and the user may use the trackball to move the second group arrow indicator 1040 to the second ultrasound image 1010.

According to an embodiment, the user may detect four objects of interest in the first ultrasound image 1020 and then additionally scan the object in order to detect one remaining object of interest. When the user examines the second ultrasound image 1010 that is a real-time scan image to find the remaining object of interest, the user may freeze the second ultrasound image 1010 and move the second group arrow indicator 1040 to the frozen second ultrasound image 1010 such that the second group arrow indicator 1040 may be placed for the remaining object of interest. When three or fewer objects of interest are detected in the first ultrasound image 1020, the second group arrow indicators 1040 numbering as many as the number of undetected objects of interest may appear on a screen, and the user may place, via the input interface, the number of the second group arrow indicators 1040 corresponding to the number of undetected objects of interest on the second ultrasound image 1010. For example, when three fingers are detected in the first ultrasound image 1020, two second group arrow indicators 1040 appear on the screen, and the user moves one of the two second group arrow indicators 1040 with a trackball and places it on the second ultrasound image 1010. After the one second group arrow indicator 1040 is placed, the remaining one second group arrow indicator 1040 moves in conjunction with the trackball, and when the remaining second group arrow indicator 1040 is placed on the second ultrasound image 1010, placement of the second group arrow indicator 1040 is finished.

Until the second group arrow indicators 1040 numbering as many as the number of objects of interest not detected in the first ultrasound image 1020 are all used thoroughly, the ultrasound imaging apparatus 300 provides a user interface that allows the second group arrow indicator 1040 to be placed on another ultrasound image. According to an embodiment, it is also possible to detect five fingers or five toes in two or more ultrasound images. For example, five fingers on one hand may be detected in first through third ultrasound images.

According to another embodiment, the ultrasound imaging apparatus 300 detects an object of interest in the second ultrasound image 1010 and automatically places an arrow indicator for the object of interest. For example, the user may obtain the second ultrasound image 1010 frozen by pressing a freeze button during an ultrasound scan, and the ultrasound imaging apparatus 300 may detect an object of interest in the second ultrasound image 1010 as the freeze button is selected and automatically place an arrow indicator corresponding to the detected object of interest.

Figure 11:
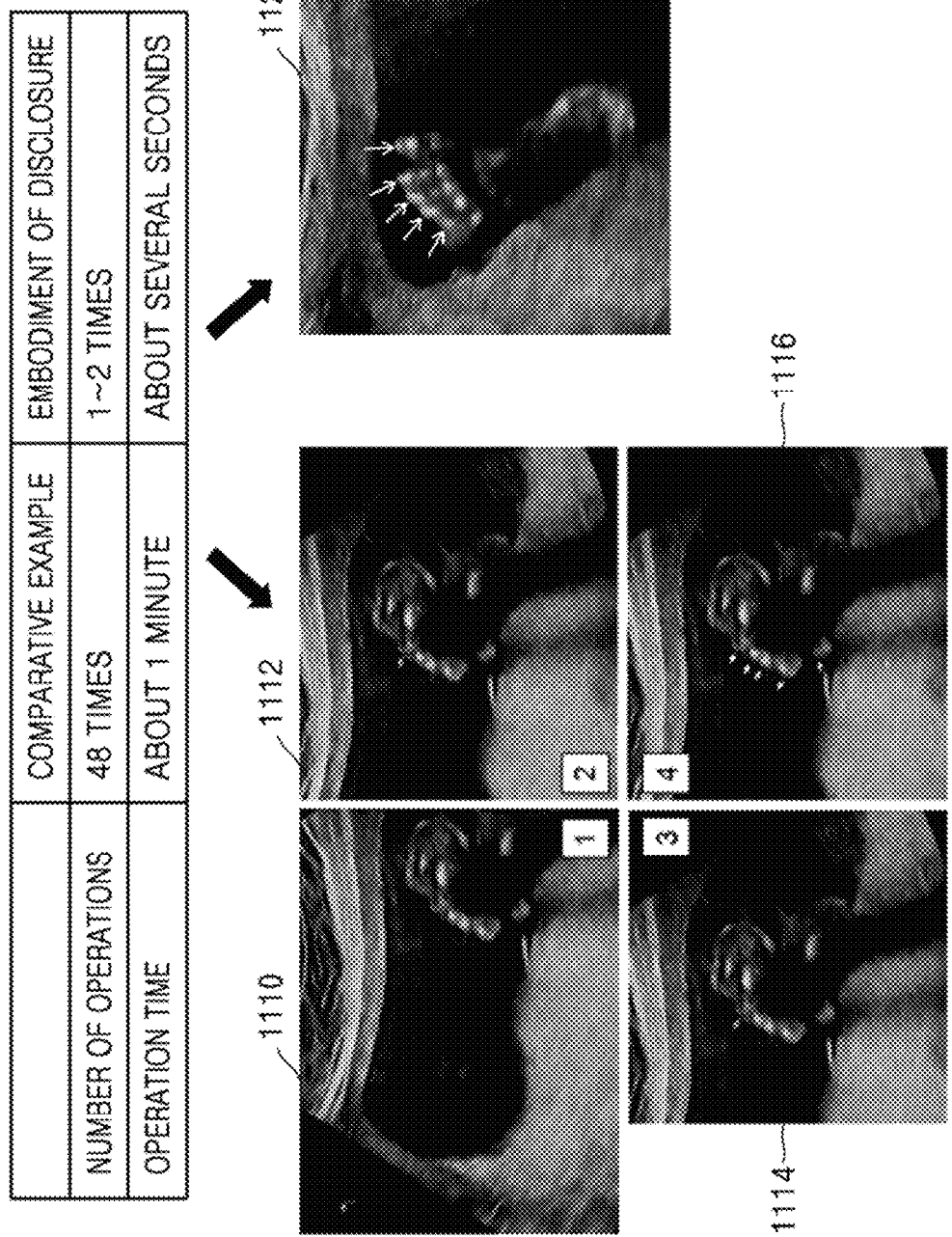
FIG. 11 illustrates the number of operations and the time required according to an embodiment of the disclosure and a comparative example.

FIG. 11 illustrates the number of operations and the time required according to an embodiment of the disclosure and a comparative example.

According to embodiments of the disclosure, by automatically detecting fingers or toes in an ultrasound image and placing an arrow indicator corresponding thereto, it is possible to significantly reduce the number of operations for placing an arrow indicator and the amount of time required for the operations. To demonstrate the effects of the embodiments of the disclosure, the number of operations and operation time will be compared with those according to the comparative example in which arrow indicators are manually placed for fingers and toes of a fetus. Such operations are performed by an experienced sonographer (hereinafter referred to as a "user") according to the comparative example, and the number of operations and the operation time may be increased according to a user's skill level.

In the comparative example, to place arrow indicators for fingers and toes, the user maps the arrow indicators to Text and Arrow buttons (first setup operation). Next, when the Arrow button is pressed, an arrow indicator appears outside an ultrasound image (1110). Then, the user moves a trackball to place an arrow indicator toward a first finger (1112). Next, the user turns an Angle button to set an angle of the arrow indicator that matches a direction of the first finger (1114). Next, the user presses the Set key to mark the arrow indicator for the first finger (1116). The operations of placing an arrow indicator (1112), setting an angle of the arrow indicator (1114), and marking the arrow indicator (1116) are repeated for the rest of the fingers. However, the user may skip the operation of setting the angle of the arrow indicator (1114) to avoid inconvenience. Even when the operation of setting the angle of the arrow indicator (1114) is omitted, the number of operations for both hands and feet reaches 48 ((2+2*4)*4). Due to the operations, it takes about 1 minute to complete the placement of arrow indicators for both hands and feet.

On the other hand, according to the embodiment of the disclosure, because arrow indicators are automatically placed on an ultrasound image only by selecting a hand/foot detection menu, the number of operations is about 1 to 2, and the operation time is only several seconds. Further, according to the embodiment of the disclosure, visibility of an arrow indicator is improved by automatically setting a direction of the arrow indicator (1120).

Figure 12:
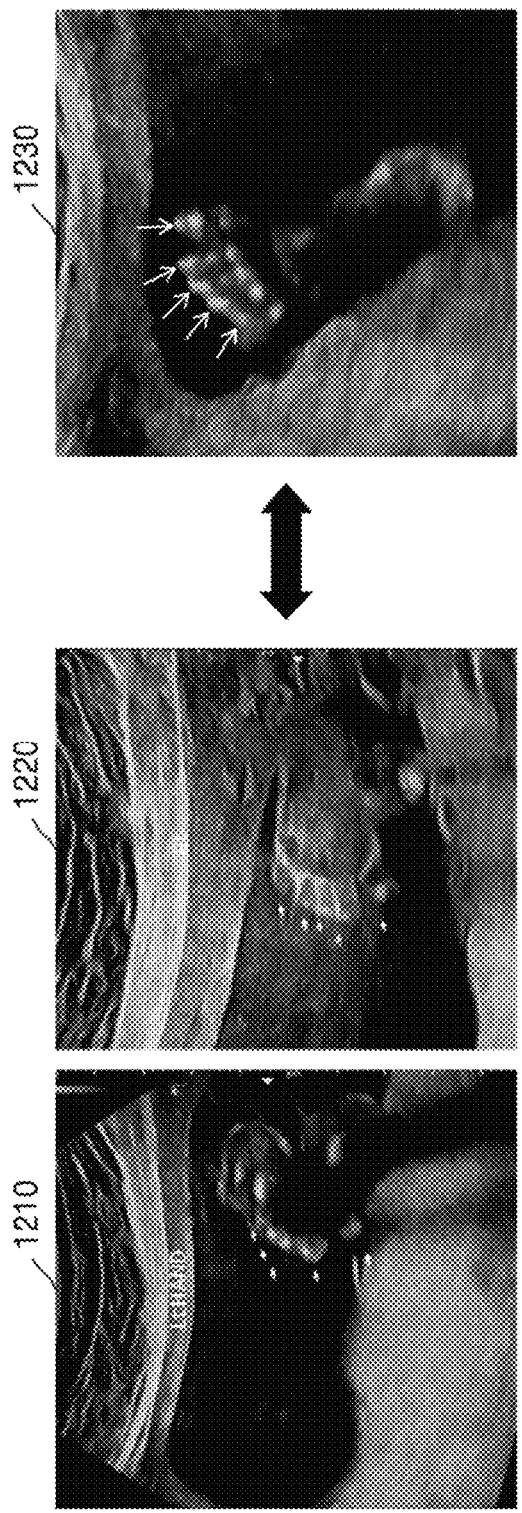
FIG. 12 is a diagram for comparing placements of arrow indicators according to an embodiment of the disclosure and a comparative example.

FIG. 12 is a diagram for comparing placements of arrow indicators according to an embodiment of the disclosure and a comparative example.

According to the embodiment of the disclosure, arrow indicators are placed in a direction perpendicular to a line connecting fingers or toes with one another, such that the arrow indicators may accurately point toward the corresponding fingers or toes (1230). On the other hand, in the comparative example, because a separate operation is required for placement of arrow indicators, this causes user inconvenience, and the user may also skip the placement of the arrow indicators. For the above reasons, as shown in ultrasound images 1210 and 1220, the arrow indicators are placed in any direction regardless of directions of fingers and toes, resulting in poor visibility of the arrow indicators.

Thus, according to embodiments of the disclosure, by automatically determining a direction of an arrow indicator and placing the arrow indicator in the direction, it is possible to significantly reduce user inconvenience and increase the visibility of the arrow indicator.

Figure 13:
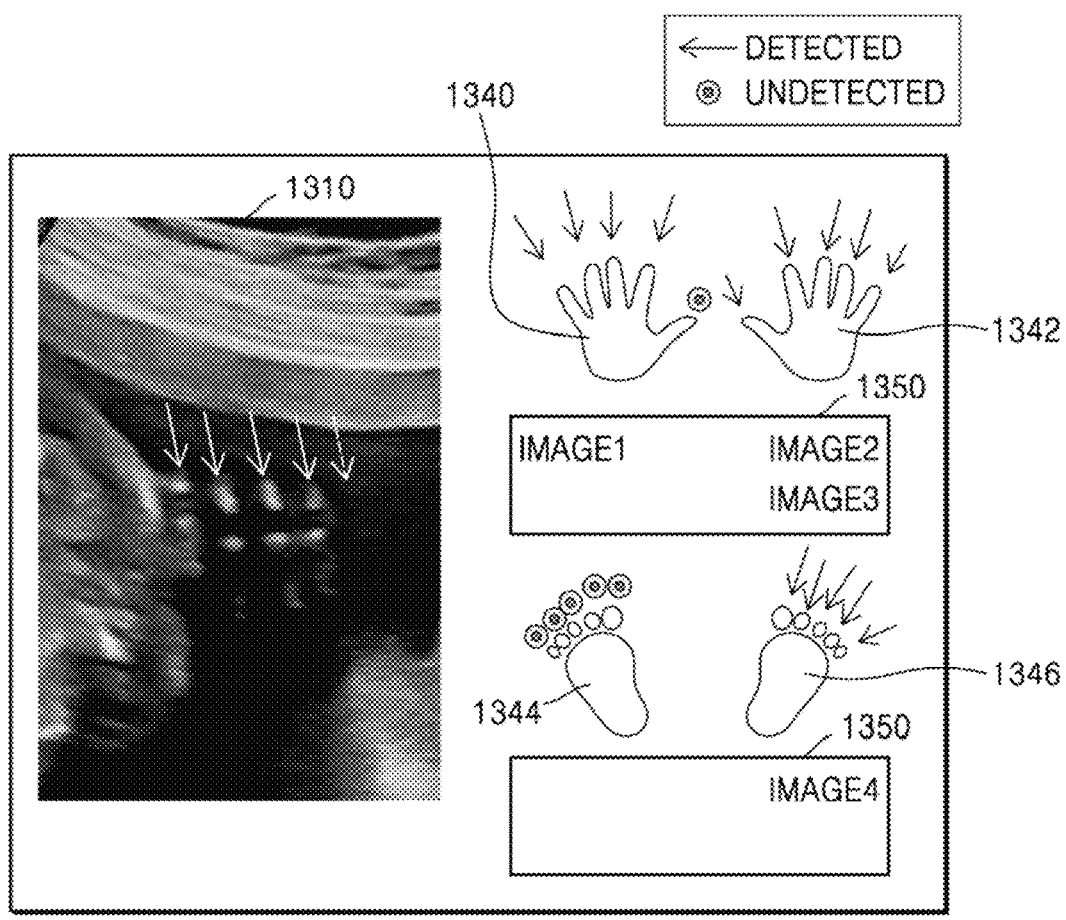
FIG. 13 illustrates a user interface according to an embodiment of the disclosure.

FIG. 13 illustrates a user interface according to an embodiment of the disclosure.

According to an embodiment of the disclosure, the ultrasound imaging apparatus 300 may provide information about an object of interest that has been detected and an object of interest that has not been detected. For example, the ultrasound imaging apparatus 300 may display left and right hands 1340 and 1342 and left and right feet 1344 and 1346 on a GUI view, and display a detected object of interest differently from an undetected object of interest. In the example of FIG. 13, an arrow indicator indicating a detected object of interest is displayed for the corresponding object of interest while a predetermined indicator indicating an undetected object of interest is displayed for the corresponding object of interest.

Furthermore, according to an embodiment of the disclosure, information 1350 about an ultrasound image in which each of the left and right hands 1340 and 1342 and the left and right feet 1344 and 1346 is detected may be displayed together on the GUI view. The information 1350 about an ultrasound image may be provided in the form of, for example, a file name, a storage path, and a thumbnail image linked to the corresponding ultrasound image.

According to an embodiment of the disclosure, information about a detected object of interest and an undetected object of interest may be provided on a GUI view in which an operation of detecting an object of interest in a first ultrasound image 1310 is performed, thereby allowing the user to easily recognize the progress of detection of the fingers and toes.

Figure 14:
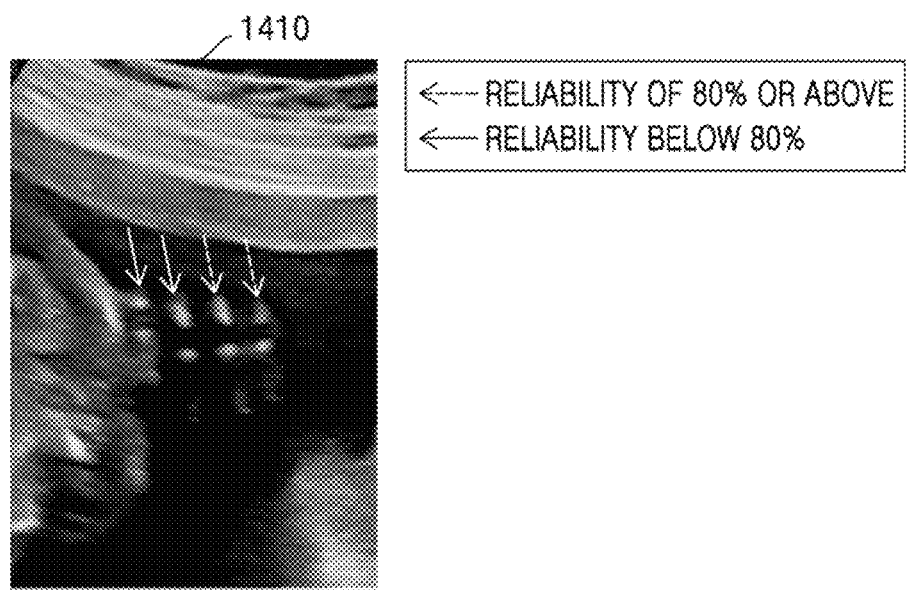
FIG. 14 illustrates an operation of providing together information about reliability of detection of an object of interest, according to an embodiment of the disclosure.

FIG. 14 illustrates an operation of providing together information about reliability of detection of an object of interest, according to an embodiment of the disclosure.

According to an embodiment of the disclosure, when detecting an object of interest, the ultrasound imaging apparatus 300 also calculates reliability information regarding the detection. The ultrasound imaging apparatus 300 may detect an object of interest by detecting a bone of a finger or toe, and misrecognition may occur due to the presence of various entities in an ultrasound image 1410. When detecting an object of interest, the ultrasound imaging apparatus 300 may calculate reliability information and output the reliability information together with an arrow indicator. According to an embodiment, reliability information may be represented by display attributes of an arrow indicator, and for example, an arrow indicator may be displayed with a different color, a different type of line, etc., according to the reliability.

The ultrasound imaging apparatus 300 may calculate reliability information by using a variety of methods. For example, the ultrasound imaging apparatus 300 may calculate reliability information based on the degree of matching between a pre-defined shape of a finger bone or toe bone and a shape of a finger bone or toe bone detected in the ultrasound image 1410.

Figure 15:
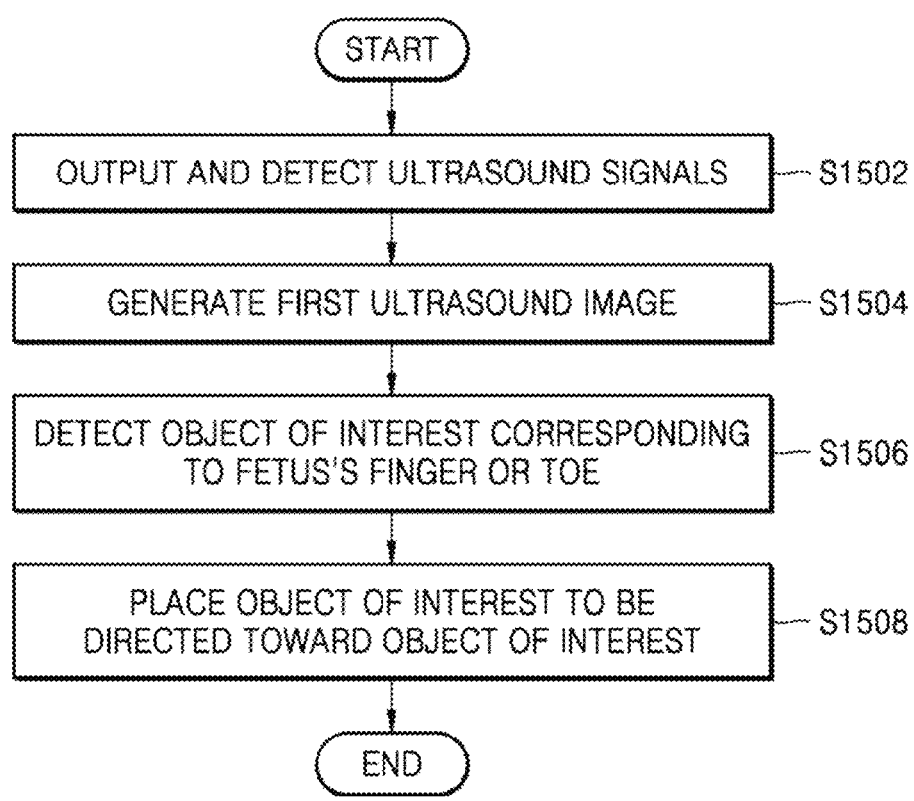
FIG. 15 is a flowchart of a method of controlling an ultrasound imaging apparatus, according to an embodiment of the disclosure.

FIG. 15 is a flowchart of a method of controlling the ultrasound imaging apparatus 300, according to an embodiment of the disclosure.

Operations of a method of controlling an ultrasound imaging apparatus according to the disclosure may be performed by various types of electronic devices including a processor. This specification mainly describes an embodiment in which the ultrasound imaging apparatus 300 performs a method of controlling an ultrasound imaging apparatus according to embodiments of the disclosure. Thus, embodiments described with respect to the ultrasound imaging apparatus 300 may be applied to embodiments described with respect to a method of controlling an ultrasound imaging apparatus. Conversely, embodiments described with respect to a method of controlling an ultrasound imaging apparatus may be applied to embodiments described with respect to the ultrasound imaging apparatus 300. Although it has been described that methods of controlling an ultrasound imaging apparatus according to embodiments of the disclosure are performed by the ultrasound imaging apparatus 300, embodiments are not limited thereto, and the methods may be performed by various types of electronic devices.

An ultrasound imaging apparatus outputs ultrasound signals to an object and detects echo signals reflected from the object (S1502).

Next, the ultrasound imaging apparatus generates a first ultrasound image based on the echo signals (S1504).

The ultrasound imaging apparatus detects an object of interest corresponding to a fetus's finger or toe in the first ultrasound image (S1506). The ultrasound imaging apparatus may detect an object of interest by detecting a shape of a finger bone or toe bone in the first ultrasound image.

Then, the ultrasound imaging apparatus places an arrow indicator to be directed toward the object of interest, and inserts the arrow indicator into the first ultrasound image (S1508). When detecting a plurality of objects of interest, the ultrasound imaging apparatus sets a line connecting the objects of interest with one another and places a plurality of arrow indicators on the first ultrasound image such that the arrow indicators are respectively directed toward the objects of interest in a direction perpendicular to the connecting line. Each arrow indicator may be placed a predetermined distance from a corresponding object of interest.

Embodiments of the disclosure may be implemented through non-transitory computer-readable recording media having stored thereon computer-executable instructions and data. The instructions may be stored in the form of program code, and when executed by a processor, generate a predetermined program module to perform a specific operation. Furthermore, when executed by the processor, the instructions may perform specific operations according to embodiments.

According to embodiments of the disclosure, an apparatus and method for automatically placing arrow indicators corresponding to a fetus's fingers and toes are provided, and accordingly, user convenience may be increased.

While embodiments of the disclosure have been particularly shown and described with reference to the accompanying drawings, it will be understood by those of ordinary skill in the art that various changes in form and details may be made therein without departing from essential characteristics or the spirit and scope of the disclosure as defined by the appended claims. The disclosed embodiments and all aspects thereof are examples only and are not to be construed as limiting the scope of the disclosure.

What is claimed is:

1. An ultrasound imaging apparatus comprising:
   a probe configured to output ultrasound signals to an object and detect echo signals reflected from the object;
   a display; and
   at least one processor configured to generate a first ultrasound image based on the echo signals, detect at least one object of interest, each corresponding to a fetus's finger or toe in the first ultrasound image, and when the at least one object of interest is detected, display, on the first ultrasound image, at least one arrow indicator outside a vicinity of a region of interest corresponding to the detected at least one object of interest, and orientate the at least one arrow indicator toward a longitude direction of the fetus's finger or toe,
   wherein the at least one object of interest comprises a plurality of objects of interest, and
   wherein the at least one processor is further configured to:
   determine a virtual line connecting the plurality of objects of interest with one another, which is not displayed on the display, and
   place the at least one arrow indicator to be respectively directed toward the plurality of objects of interest in a direction perpendicular to the virtual line.

2. The ultrasound imaging apparatus of claim 1, wherein the at least one processor is further configured to detect the at least one object of interest by detecting a shape of a finger bone or toe bone in the first ultrasound image.

3. The ultrasound imaging apparatus of claim 1, wherein the at least one processor is further configured to recognize fingers that are the at least one object of interest when four or more shapes of finger bones are detected in the first ultrasound image and recognize toes that are the at least one object of interest when four or more shapes of toe bones are detected in the first ultrasound image.

4. The ultrasound imaging apparatus of claim 1, wherein the at least one processor is further configured to place the at least one arrow indicator on a region corresponding to an amniotic fluid in the first ultrasound image.

5. The ultrasound imaging apparatus of claim 1, wherein the at least one processor is further configured to place, when four fingers or four toes are recognized in the first ultrasound image, a fifth arrow indicator in a direction of a thumb or big toe.

6. The ultrasound imaging apparatus of claim 1, wherein the at least one processor is further configured to control the display to display the first ultrasound image and a second ultrasound image on the display, detect at least one object of interest in the second ultrasound image when four or fewer objects of interest are detected in the first ultrasound image, and place the at least one arrow indicator for the at least one object of interest detected in the second ultrasound image.

7. The ultrasound imaging apparatus of claim 1, further comprising an input interface,
   wherein the at least one processor is further configured to display the first ultrasound image and a second ultrasound image on the display, display on the first ultrasound image, when four or fewer objects of interest are detected in the first ultrasound image, first group arrow indicators respectively corresponding to the four or fewer objects of interest detected in the first ultrasound image and a second group arrow indicator visually represented in a different way from the first group arrow indicators, and place the second group arrow indicator onto the second ultrasound image based on a user input for moving the second group arrow indicator, the user input being received via the input interface.

8. The ultrasound imaging apparatus of claim 1, wherein the at least one processor is further configured to provide, via the display, information about whether each of five (5) fingers on left and right hands and each of five (5) toes on left and right feet have been recognized.

9. The ultrasound imaging apparatus of claim 1, wherein the at least one processor is further configured to calculate information about reliability in detecting the at least one object of interest and display on the display the information about reliability of the at least one arrow indicator together with the at least one arrow indicator.

10. A method of controlling an ultrasound imaging apparatus, the method comprising:
    outputting ultrasound signals to an object and detecting echo signals reflected from the object;
    generating a first ultrasound image based on the echo signals;
    detecting at least one object of interest, each corresponding to a fetus's finger or toe in the first ultrasound image;
    when the at least one object of interest is detected, displaying, on the first ultrasound image, at least one arrow indicator outside a vicinity of a region of interest corresponding to the detected at least one object of interest, and orientating the at least one arrow indicator toward a longitude direction of the fetus's finger or toe,
    wherein the at least one object of interest comprises a plurality of objects of interest, and
    wherein the placing of the at least one arrow indicator comprises:
    determining a virtual line connecting the plurality of objects of interest with one another, which is not displayed on the display, and
    placing the at least one arrow indicator to be respectively directed toward the plurality of objects of interest in a direction perpendicular to the virtual line.

11. The method of claim 10, wherein the detecting of the at least one object of interest comprises detecting the at least one object of interest by detecting a shape of a finger bone or toe bone in the first ultrasound image.

12. The method of claim 10, wherein the detecting of the at least one object of interest comprises:
    recognizing fingers that are the at least one object of interest when four or more shapes of finger bones are detected in the first ultrasound image; and
    recognizing toes that are the at least one object of interest when four or more shapes of toe bones are detected in the first ultrasound image.

13. The method of claim 10, wherein the placing of the at least one arrow indicator comprises placing the at least one arrow indicator on a region corresponding to an amniotic fluid in the first ultrasound image.

14. The method of claim 10, wherein the placing of the at least one arrow indicator comprises placing, when four fingers or four toes are recognized in the first ultrasound image, a fifth arrow indicator in a direction of a thumb or big toe.

15. The method of claim 10, further comprising:
displaying the first ultrasound image and a second ultrasound image; and
detecting at least one object of interest in the second ultrasound image when four or fewer objects of interest are detected in the first ultrasound image and placing the at least one arrow indicator for the at least one object of interest detected in the second ultrasound image.

16. The method of claim 10, further comprising:
displaying the first ultrasound image and a second ultrasound image;
displaying on the first ultrasound image, when four or fewer objects of interest are detected in the first ultrasound image, first group arrow indicators respectively corresponding to the four or fewer objects of interest detected in the first ultrasound image and a second group arrow indicator visually represented in a different way from the first group arrow indicators; and
placing the second group arrow indicator on the second ultrasound image based on a user input for moving the second group arrow indicator.

17. The method of claim 10, further comprising displaying information about whether each of five (5) fingers on left and right hands and each of five (5) toes on left and right feet have been recognized.

18. A computer program stored in a non-transitory computer-readable recording medium and comprising at least one instruction which, when executed by a processor, causes the processor to perform the method comprising:
outputting ultrasound signals to an object and detecting echo signals reflected from the object;
generating a first ultrasound image based on the echo signals;
detecting at least one object of interest, each corresponding to a fetus's finger or toe in the first ultrasound image;
when the at least one object of interest is detected, placing displaying, on the first ultrasound image, at least one arrow indicator outside a vicinity of a region of interest corresponding to the detected at least one object of interest, and orientating the at least one arrow indicator toward a longitude direction of the fetus's finger or toe,
wherein the at least one object of interest comprises a plurality of objects of interest, and
wherein the placing of the at least one arrow indicator comprises:
determining a virtual line connecting the plurality of objects of interest with one another, which is not displayed on the display, and
placing the at least one arrow indicator to be respectively directed toward the plurality of objects of interest in a direction perpendicular to the virtual line.

* * * * *